United States Patent [19]

deWitt et al.

[11] 4,254,053
[45] Mar. 3, 1981

[54] PROCESS FOR MANUFACTURING D CAMPHORATE OF L CARNITINAMIDE AND D CAMPHORATE OF D CARNITINAMIDE

[75] Inventors: Paolo deWitt; Enrico Diamanti, both of Rome, Italy

[73] Assignee: Claudio Cavazza, Rome, Italy

[21] Appl. No.: 55,238

[22] Filed: Jul. 6, 1979

[30] Foreign Application Priority Data

Jul. 10, 1978 [IT] Italy .............................. 50222 A/78

[51] Int. Cl.$^3$ .............................................. C07C 91/26
[52] U.S. Cl. .................................. 260/501.15; 564/198
[58] Field of Search ........................................ 260/501.15

[56] References Cited

U.S. PATENT DOCUMENTS 3,632,623  1/1972  Becke et al. ................ 260/501.15 X

OTHER PUBLICATIONS

Binon et al., Chem. Absts. 67, 64703(x), 1967.
Marly, "Chem. Absts., 64, 11314(e), 1966.
Mueller et al., Hoppe-Seyler's Z. Physiol. Chem., 353(4), 618–622, 1972.

*Primary Examiner*—Natalie Trousof
*Assistant Examiner*—G. T. Breitenstein
*Attorney, Agent, or Firm*—Ladas & Parry

[57] ABSTRACT

A process for manufacturing the D camphorate of L carnitinamide and the D camphorate of D carnitinamide is disclosed, wherein D,L carnitinamide hydrochloride is converted to D,L carnitinamide free base which directly reacts with D camphoric acid either as an aqueous suspension or in solid form, thus obtaining a solution of D camphorate of D,L carnitinamide. The resolution of the optical isomers is achieved by drying this solution and taking up the residue with isopropanol, whereupon the D camphorate of L carnitinamdide crystallizes out of the isopropanol solution and the D camphorate of D carnitinamide remains in solution.

9 Claims, No Drawings

4,254,053

PROCESS FOR MANUFACTURING D CAMPHORATE OF L CARNITINAMIDE AND D CAMPHORATE OF D CARNITINAMIDE

BACKGROUND OF THE INVENTION

1. Field of the Invention

The present invention relates to a new industrial process for the preparation of D camphorate of L carnitinamide and D camphorate of D carnitinamide.

2. Description of the Prior Art

As known, for instance from the Belgian Pat. No. 660039, the D camphorates of L and D carnitinamide are key intermediates in the preparation of useful therapeutic agents. For instance, the D Camphorate of L carnitinamide can be converted to L-carnitinamide which exhibits remarkable stimulating respiratory activity. Moreover, L-carnitinamide as well as D carnitinamide can be used for the industrial production of laevorotatory and dextrorotatory carnitine hydrochloride respectively, which are also known, useful therapeutic agents.

The previously proposed processes for the production of laevorotatory and dextrorotatory carnitine hydrochloride may be divided into two groups; processes that use the hydrochloride of DL Carnitine nitrile as the starting compound, and a process using the hydrochloride of DL Carnitinamide as the starting compound.

The first group, namely, processes using the hydrochloride of D, L carnitine nitrile are chronologically those proposed by E. STRACK et al. (Z. Physiol. Chem. 318, 129, 1960), HORIUCHI et al. (TOKIO KOHO SHO 40-3891), AYATA (YAKUGAKU ZASSHI 81, 778, 1961) and T. DOHI et al. (Japan Pat. No. 63291/1965 of the OTSUKA Pharmaceutical Co.).

In general, it has been demonostrated that these methods are not economically feasible for the industrial production of L carnitine chloride since some of them are based upon a double formation of salts in order to achieve the separation of the laevorotatory isomer (method proposed by E. STRACK and method proposed by AYATA), while the other two methods comprise the use of particularly expensive acids, such as L-camphorsulfonic acid (HORIUCHI et al.) and D acetylglutamic acid (T. DOHI et al.).

Moreover, the use of the nitrile of carnitine is not advisable for this type of resolution since the method for preparing the nitrile involves the attainment of a compound with a high number of salt impurities (10–15%) which are not easily separable; such impurities considerably complicate the resolution process of the two optical antipodes.

Furthermore, in the successive hydrolysis of the optically active carnitine nitrile to Carnitinamide and thence to carnitine, racemization phenomena may occur. This untoward effect takes place especially in the conversion to carnitinamide and, therefore, the final compound that is obtained does not have the desired optical purity.

The second group of processes which use racemic carnitinamide as the starting compound has the advantage of utilizing an easily available compound, which has a high degree of purity and is easily hydrolyzable to carnitine without danger of racemization.

The process using carnitinamide hydrochloride as the starting compound for resolution is disclosed in the above-mentioned Belgian Pat. No. 660039. Such a process comprises the use of D camphoric acid, which is also easily available at a low price, for producing the D camphorate of D,L carnitinamide.

However, this process presents a serious drawback and, consequently, finds little industrial application since, in order to form the D camphorate of D,L carinitinamide, it is first necessary to form the ammonium salt of D camphoric acid with ammonia; the ammonium D camphorate that is formed is then converted to silver D Camphorate by the action of silver nitrate. Since the carnitinamide is in the hydrochloride salt form, the formation of this silver salt is essential in order to eliminate the chloride ion. Such a process is, therefore, very expensive (because of the imperative use of the silver compound) and difficult to carry out industrially in that the various steps of the process have to be carried out away from the light in order to avoid marked blackening of the reaction vessels, due to the large quantity of AgCl which is formed. The final compound may in addition be rendered impure by the presence of silver ions.

SUMMARY OF THE INVENTION

It is, therefore, an object of the present invention to provide a process for the industrial preparation of the D camphorate of L carnitinamide and the D camphorate of D carnitinamide, which does not have the serious drawbacks of the prior art processes.

A more specific object of the present invention is to provide a process less expensive and time-consuming than the prior art processes for producing on an industrial scale the D-camphorate of L carnitinamide and the D-camphorate of D carnitinamide.

More particularly, it is an object of the present invention to provide such a process, wherein the use of the expensive and troublesome silver compounds is totally avoided.

It is a further object of the present invention to provide such a process wherein the starting materials are the inexpensive and readily available D,L-carnitinamide hydrochloride and D-camphoric acid which heretofore have necessarily called for the use of the silver compounds in order to give the desired products.

It has been, in fact, surprisingly found that previous preparation of silver camphorate is not actually necessary and that the D-camphoric acid can be reacted directly with D,L-carnitinamide, provided that this latter compound is in its free base form and not in its hydrochloride salt form.

According to the invention, the process for producing the D camphorate of L carnitinamide and the D camphorate of D carnitinamide comprises:

(1) converting a solution of D,L carnitinamide hydrochloride to a solution of D,L carnitinamide free base;

(2) reacting the D,L carnitinamide free base solution directly with D-camphoric acid, thus obtaining a solution of D-camphorate of D,L carnitinamide;

(3) drying the solution of step (2) and taking up the residue with a lower alkanol having from 1 to 5 carbon atoms, to form an alcoholic solution, whereupon a solid phase comprising the D-camphorate of L-carnitinamide crystallizes out of the alcoholic solution; and (4) separating said solid phase from the alcoholic solution comprising the D camphorate of D-carnitinamide.

DESCRIPTION OF THE PREFERRED EMBODIMENTS

Preferably, the step of converting the solution of D,L-carnitinamide hydrochloride to a solution of D,L-carnitinamide free base is carried out by contacting an aqueous solution of D,L carnitinamide hydrochloride with either strongly acidic or strongly basic ion exchange resins.

It has been found that the "Gel" type AMBERLITE ion exchange resins manufactured by Rohm & Haas are particularly suitable in the process of the present invention. Specific, non limiting examples of such AMBERLITE ion exchange resins are the resins IRA 402, IRA 410 and IRA 401/S.

By using the ion exchange resins of the basic type the DL carnitinamide free base passes directly without being retained, whereas the chloride ion is fixed by the resin. Conversely by using ion exchange resins of the acid type the DL carnitinamide is fixed, and it is then possible, by treatment of the resin having fixed thereon the DL carnitinamide with D camphoric acid solution to elute DL carnitinamide in the form of D camphorate salt.

Such ion exchange resins can be used either directly on the solution of DL carnitinamide hydrochloride or by the use of columns. In general it is preferred to resort to the latter system in that the process is thus more easily controllable, and the resins deteriorate less during regeneration.

Once the resins have been used, they can in act be easily regenerated in known per se manners, and, therefore, they can be used for a practically unlimited number of operations.

The average bead size of the ion exchange resins vary preferably from 0.39 to 0.46 mm.

The preferred way of operating would be by using ion exchange resins of the strongly basic type, packed in a chromatographic column and causing the D,L-carnitinamide hydrochloride-containing solution to pass through the column.

The residence time of the solution in the column should be from 30 to 60 minutes.

The preferred range of concentration of the solution passing through the column is 500 grams of D,L-carnitinamide hydrochloride in 1,5-3 liters of solvent, preferably water.

The temperature of the solution passing through the column can vary from 15° to 60° C., the room temperature being preferred.

Because of the instability of the D,L-carnitinamide free base contained in the solution leaving the bottom of the chromatographic column (the carnitinamide tends to undergo hydrolysis to carnitine), the preferred way of operating is by directly feeding the solution leaving the column to the reaction vessel containing the D camphoric acid. However, the solution might be allowed to stand for about 0.5-1 hour before reacting it with the D-camphoric acid, without substantial danger of hydrolysis.

The D-camphoric acid can be used either in suspension form in a suitable suspension medium, preferably water, or in solid form. The latter is preferred because in the subsequent step of reducing the volume of the reaction mixture to dryness under vacuum, lesser amount of water is to be evaporated and, consequently, less energy is required.

After reducing the reaction mixture to dryness, the resulting residue is taken up with a lower alkanol having from 1 to 5 carbon atoms, isopropanol being particularly preferred.

The resolution of the optical isomers is achieved by allowing the alcoholic solution to stand for about 2-8 hours, a substantially pure solid phase of D-camphorate of L-carnitinamide crystallizes out of the solution, whereas the D-camphorate of D carnitinamide remains in solution.

After separating (e.g. by filtration) the solid phase from the liquid phase, the solid phase can be recrystallized from the same alcohol used for taking up the residue. If isopropanol is used, a simple washing with isopropanol is sufficient to give a high purity product.

The following examples will further illustrate the invention, without limiting its scope.

EXAMPLE 1

Preparation of L(−) Carnitinamide hydrochloride 500 g of DL Carnitinamide hydrochloride are dissolved in 2000 ml of distilled water and then passed through a chromatographic glass column (diameter 50 mm, height 1.50 m) packed with 4,000 ml of ion exchange resin of the basic type (IRA 402 or IRA 410 or IRA 401/S etc. ROHM & HAAS) activated in OH⁻ form. The residence time of the solution in the column is 30 minutes. The solution is at room temperature. The alkaline solution coming out of the column is collected directly in a vessel containing 550 g of D camphoric acid suspended in 1,200 ml of distilled water. As the DL carnitinamide free base percolates through the column and reacts with the D camphoric acid the latter is solubilized. At the end of the passage of DL carnitinamide through the column (pH of the solution approx. 5-6) all of the D camphoric acid will have solubilized.

The aqueous solution containing the D camphorate of DL carnitinamide is at this point concentrated to dryness in vacuo, taken up twice with 300 ml of isopropyl alcohol and then 4,300 ml of isopropyl alcohol containing 10 g of dissolved D camphoric acid are finally added.

In these conditions, after standing overnight at 0° C., 420 g of a white compound crystallizes and this constitutes the D camphorate of L carnitinamide having $[\alpha]_D^{20} = +10$ (c=2% in H$_2$O), which after a successive crystallization from isopropanol yields 360 g of the compound at $[\alpha]_D^{20} = +7.8$. These 360 g of D camphorate of L carnitinamide are suspended in 3,000 cc of isopropanol and then treated with gaseous HCl up to an acid reading of the isopropanol. After standing at −4° C. for approximately 12 hours, an abundant precipitate of L(−) carnitinamide hydrochloride is obtained, this is then filtered and dried in vacuo at 40° C. yielding 150 g of dry compound $[\alpha]_D^{20} = -18$ (c=2 in H$_2$O).

M.P. = 239°-241° C.

L-carnitinamide chloride has the following NMR:

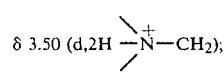

-continued

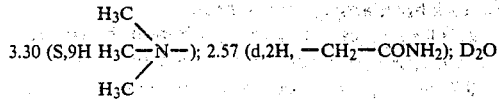
3.30 (S,9H H$_3$C—N—); 2.57 (d,2H, —CH$_2$—CONH$_2$); D$_2$O

EXAMPLE 2

Preparation of L(−) carnitinamide hydrochloride

The procedures of Example 1 are repeated, except that the D,L-carnitinamide free base-containing solution coming out of the chromatography column is fed directly into a reaction vessel containing solid D camphoric acid.

EXAMPLE 3

Preparation of L(−) carnitine hydrochloride 150 g of L(−) carnitinamide hydrochloride are dissolved in 310 ml of distilled water and heated to 98°–100° C. Then, 326 g of oxalic acid are added and the mixture kept under stirring for 6 hours maintaining the temperature constant.

The mixture is then allowed to cool for 12 hours and the ammonium oxalate precipitate is filtered off. The filtered solution is concentrated to dryness, the solid residue taken up twice the isopropyl alcohol and then crystallized at 0° C.; 110 g of the compound is obtained having $[\alpha]_D^{20} = -25$ (c=5 in H$_2$O). All the chemical-physical characteristics of the compound thus obtained (MP, IR, NMR and elementary analysis) are in conformity with those of known L(−) carnitine hydrochloride.

$M.P. = 140°-142°$ C.

L-carnitinamide hydrochloride has the following NMR:

δ 3.57 (d,2H —N—CH$_2$);

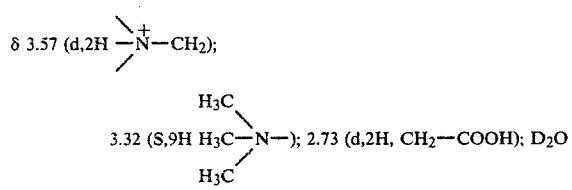
3.32 (S,9H H$_3$C—N—); 2.73 (d,2H, CH$_2$—COOH); D$_2$O

EXAMPLE 4

Preparation of D(+) carnitinamide hydrochloride

Through a chromatographic glass column (height 120 cm, diameter 40 mm) packed with 1.35 kg of ion exchange resin of the basic type (IRA 402 or IRA 401/S or IRA 410, etc. ROHM & HAAS) activated in the OH$^-$ form, is passed an aqueous solution containing 160 g of DL carnitinamide hydrochloride in 700 ml of distilled water. The residence time of the solution in the column is 1 hour. The solution is at room temperature.

The solution coming out of the column and containing DL carnitinamide as a free base is added directly to 185 g of D camphoric acid suspended in 400 ml of water. After filtration the aqueous solution is concentrated to dryness, taken up with isopropyl alcohol and allowed to crystallize for 24 hours at 0° C. The crystalline solid containing D camphorate of L (−) carnitinamide is then filtered and processed as per example 1, while the another 20 g of D camphoric acid is added to the solution and allowed to crystallize for a further 24 hours in isopropanol. The resultant solid compound is filtered and the clear solution is bubbled with cold gaseous HCl until a distinct acid reaction is obtained. After standing in a freezer for 12 hours at −4° C., 45 g of white microcrystalline compound at $[\alpha]_D^{20} = +17.0$ having the chemical-physical characteristics (IR, NMR, MP and elementary analysis) in conformity with those of D (+) carnitinamide hydrochloride are obtained.

EXAMPLE 5

Preparation of D (+) carnitine hydrochloride 45 g of D (+) carnitinamide hydrochloride are dissolved in 100 ml of water, heated to boiling point and then treated with 96 grams of oxalic acid for 6 hours under continuous stirring. The solution is then cooled for 12 hours at 0° C.; the ammonium oxalate which formed is filtered, and the clear solution concentrated to dryness in vacuo. The solid is washed well with isopropyl alcohol and then crystallized with the same solvent. 30 g of the compound are obtained at $[\alpha]_D^{20} = +23.6$ (c=5 in H$_2$O) having the chemical-physical characteristics (IR, NMR, MP and elementary analysis) in conformity with those of D (+) carnitine hydrochloride.

The following example illustrates the racemization of D carnitinamide to D, L carnitine hydrochloride which is then converted to D, L carnitinamide hydrochloride for subsequent resolution of the L and D optical isomers.

EXAMPLE 6

Step (a): Preparation of D, L carnitine hydrochloride 45 g of D carnitinamide hydrochloride (as prepared in Example 4) are dissolved in 200 cc of conc. HCl and allowed to stand at 100° C. for 60 hours. The solution is concentrated to dryness under vacuum. The residue (about 45 g) is D, L carnitine hydrochloride. In fact, the residue shows $[\alpha]_D^{20} = 0$ whereas its melting point and NMR correspond to those of known D, L carnitine hydrochloride.

Step (b): Preparation of D, L carnitinamide free base 10 g of D, L carnitine hydrochloride are suspended in 100 cc of absolute ethyl alcohol. The resulting suspension is saturated at 0° C. with gaseous HCl. Subsequently, the suspension is heated at the reflux temperature until dissolution of the solid phase is achieved, which takes approximately three hours. The resulting solution is concentrated under vacuum, thus obtaining 10 grams of carnitine ethyl ester. This carnitine ethyl ester is treated with 100 cc. of 25% NH$_4$OH for 40 hours at room temperature. The solution is concentrated to dryness under vacuum and the residue is D,L carnitinamide hydrochloride (12 g) comprising about 10% of NH$_4$Cl.

This D,L carnitinamide hydrochloride is treated as in Example 1, i.e., converted to D,L carnitinamide free base and reacted with D camphoric acid for resolution of the optical isomers.

What is claimed is:

1. In a process for producing the D-camphorate of L-carnitinamide and the D-camphorate of D-carnitinamide comprising the preparation of the D-camphorate of D,L-carnitinamide from a silver salt of D-camphoric acid and D,L-carnitinamide hydrochloride, forming an alcoholic solution of said camphorate with a lower alkanol having from 1 to 5 carbon atoms and separating the solid phase comprising the D-camphorate of L-carnitinamide from the alcoholic solution,
the improvement whereby
(a) an aqueous solution of D,L-carnitinamide free base is prepared by contacting a solution of D,L-carnitinamide hydrochloride with a strongly acidic or strongly basic ion exchange resin and
(b) substantially directly after said free base solution is prepared contacting said free base solution with D-camphoric acid to form the D-camphorate of D,L-carnitinamide.

2. The process of claim 1, wherein the ion exchange resin is selected from the group consisting of strongly basic and strongly acidic AMBERLITE resins.

3. The process of claim 2, wherein said resin is packed in a chromatographic column.

4. The process of claim 3, wherein the residence time of said solution in said column is from 30 to 60 minutes.

5. The process of claim 3, wherein the concentration of said solution is 500 grams of D,L-carnitinamide hydrochloride in 1.5–3 liters of a solvent therefor.

6. The process of claim 1 wherein the D-camphoric acid is in suspension form.

7. The process of claim 1 wherein the D-camphoric acid is in solid form.

8. The process of claim 1 wherein said lower alkanol having from 1 to 5 carbon atoms is isopropanol.

9. The process of claim 1, wherein the aqueous solution of D,L-carnitinamide free base is 100% aqueous.

* * * * *